United States Patent
Eidenschink et al.

(10) Patent No.: US 8,550,986 B2
(45) Date of Patent: Oct. 8, 2013

(54) PROPELLABLE APPARATUS WITH ACTIVE SIZE CHANGING ABILITY

(75) Inventors: Tracee E Eidenschink, Wayzata, MN (US); John J. Allen, Mendota Heights, MN (US)

(73) Assignee: FUJIFILM Corporation, Tokyo (JP)

( * ) Notice: Subject to any disclaimer, the term of this patent is extended or adjusted under 35 U.S.C. 154(b) by 328 days.

(21) Appl. No.: 12/881,793

(22) Filed: Sep. 14, 2010

(65) Prior Publication Data

US 2011/0065988 A1    Mar. 17, 2011

Related U.S. Application Data

(60) Provisional application No. 61/243,208, filed on Sep. 17, 2009.

(51) Int. Cl.
*A61B 1/04* (2006.01)
(52) U.S. Cl.
USPC ............ 600/115; 600/114; 600/127; 600/129
(58) Field of Classification Search
USPC ........................ 600/110, 114, 116, 127, 129
See application file for complete search history.

(56) References Cited

U.S. PATENT DOCUMENTS

| | | | |
|---|---|---|---|
| 2,264,638 A * | 12/1941 | Orr | ............................... 137/223 |
| 3,797,445 A | 3/1974 | Zeimer | |
| 4,117,847 A | 10/1978 | Clayton | |
| 4,176,662 A | 12/1979 | Frazer | |
| 4,207,872 A | 6/1980 | Meiri et al. | |
| 4,305,386 A | 12/1981 | Tawara | |
| 4,368,739 A | 1/1983 | Nelson, Jr. et al. | |
| 4,558,971 A | 12/1985 | David | |
| 4,561,427 A | 12/1985 | Takada | |
| 4,600,939 A | 7/1986 | Sluyter et al. | |
| 4,776,845 A | 10/1988 | Davis | |

(Continued)

FOREIGN PATENT DOCUMENTS

| DE | 10012560 | 9/2001 |
|---|---|---|
| JP | 55-045427 A | 3/1980 |

(Continued)

OTHER PUBLICATIONS

"International Application Serial No. PCT/US2010/002496, International Search Report mailed Nov. 12, 2010", 7 pgs.

(Continued)

*Primary Examiner* — Katherine Dowe
*Assistant Examiner* — Aaron B Fairchild
(74) *Attorney, Agent, or Firm* — Sughrue Mion, PLLC

(57) ABSTRACT

A propellable apparatus comprises one or more rotatable membranes. The rotatable membranes include an inner surface at least partially defining an encircled region and a continuous outer surface that turns outward to engage a cavity or lumen wall, for example, and turns inward to at least partially encompass a central region defining a longitudinal path. The membranes are powerable to provide movement relative to the cavity or lumen wall. The apparatus further comprises an inflatable and deflatable support structure, configured to bias the outer surface of the membranes outward to engage the cavity or lumen wall at a first outer diameter, and be deformable inward in response to a compressive force or operator command to provide a second outer diameter that is less than the first outer diameter. In some examples, the rotatable membranes include belt-like membranes, and the inflatable and deflatable support structure includes at least one impermeable bladder.

11 Claims, 6 Drawing Sheets

(56) References Cited

U.S. PATENT DOCUMENTS

| | | | |
|---|---|---|---|
| 4,866,516 A | 9/1989 | Hibino et al. |
| 4,874,364 A | 10/1989 | Morris et al. |
| 5,259,366 A | 11/1993 | Reydel et al. |
| 5,331,975 A | 7/1994 | Bonutti |
| 5,419,312 A | 5/1995 | Arenberg et al. |
| 5,429,609 A | 7/1995 | Yoon |
| 5,441,486 A | 8/1995 | Yoon |
| 5,562,601 A | 10/1996 | Takada |
| 5,571,114 A | 11/1996 | Devanaboyina |
| 5,575,754 A | 11/1996 | Konomura |
| 5,595,565 A | 1/1997 | Treat et al. |
| 5,620,408 A | 4/1997 | Vennes et al. |
| 5,662,587 A | 9/1997 | Grundfest et al. |
| 5,702,418 A | 12/1997 | Ravenscroft |
| 5,782,817 A | 7/1998 | Franzel et al. |
| 5,819,736 A | 10/1998 | Avny et al. |
| 5,865,802 A | 2/1999 | Yoon et al. |
| 5,951,466 A | 9/1999 | Segermark et al. |
| 6,007,482 A | 12/1999 | Madni et al. |
| 6,038,488 A | 3/2000 | Barnes et al. |
| 6,071,233 A | 6/2000 | Ishikawa et al. |
| 6,071,234 A | 6/2000 | Takada |
| 6,077,219 A | 6/2000 | Viebach et al. |
| 6,086,603 A | 7/2000 | Termin et al. |
| 6,149,581 A | 11/2000 | Klingenstein |
| 6,162,171 A | 12/2000 | Ng et al. |
| 6,171,316 B1 | 1/2001 | Kovac et al. |
| 6,224,544 B1 | 5/2001 | Takada |
| 6,240,312 B1 | 5/2001 | Alfano et al. |
| 6,309,346 B1 | 10/2001 | Farhadi |
| 6,315,713 B1 | 11/2001 | Takada |
| 6,321,121 B1 | 11/2001 | Zelickson et al. |
| 6,409,727 B1 | 6/2002 | Bales et al. |
| 6,436,107 B1 | 8/2002 | Wang et al. |
| 6,450,949 B1 | 9/2002 | Farkas et al. |
| 6,461,294 B1 | 10/2002 | Oneda et al. |
| 6,461,295 B2 | 10/2002 | Takada |
| 6,463,361 B1 | 10/2002 | Wang et al. |
| 6,468,203 B2 | 10/2002 | Belson |
| 6,485,409 B1 | 11/2002 | Voloshin et al. |
| 6,508,188 B2 | 1/2003 | Dong et al. |
| 6,517,477 B1 | 2/2003 | Wendlandt |
| 6,522,906 B1 | 2/2003 | Salisbury, Jr. et al. |
| 6,537,206 B2 | 3/2003 | Takada |
| 6,604,004 B1 | 8/2003 | Zelickson et al. |
| 6,648,814 B2 | 11/2003 | Kim et al. |
| 6,663,598 B1 | 12/2003 | Carrillo, Jr. et al. |
| 6,695,771 B2 | 2/2004 | Takada |
| 6,699,179 B2 | 3/2004 | Wendlandt |
| 6,702,735 B2 | 3/2004 | Kelly |
| 6,761,717 B2 | 7/2004 | Bales et al. |
| 6,764,441 B2 | 7/2004 | Chiel et al. |
| 6,767,339 B2 | 7/2004 | Reydel |
| 6,824,510 B2 | 11/2004 | Kim et al. |
| 6,866,626 B2 | 3/2005 | Long et al. |
| 6,971,990 B2 | 12/2005 | Ziegler et al. |
| 7,044,245 B2 | 5/2006 | Anhalt et al. |
| 7,087,011 B2 | 8/2006 | Cabiri et al. |
| 7,235,046 B2 | 6/2007 | Anhalt et al. |
| 7,387,179 B2 | 6/2008 | Anhalt et al. |
| 7,736,300 B2 | 6/2010 | Ziegler et al. |
| 2001/0008952 A1 | 7/2001 | Takada |
| 2001/0041874 A1 | 11/2001 | Reydel |
| 2001/0044595 A1 | 11/2001 | Reydel et al. |
| 2002/0049365 A1 | 4/2002 | Takada |
| 2002/0107478 A1 | 8/2002 | Wendlandt |
| 2002/0117097 A1 | 8/2002 | Dong et al. |
| 2002/0143237 A1 | 10/2002 | Oneda et al. |
| 2002/0156347 A1 | 10/2002 | Kim et al. |
| 2002/0156454 A1 | 10/2002 | Reydel |
| 2002/0173700 A1 | 11/2002 | Kim et al. |
| 2003/0060680 A1 | 3/2003 | Wendlandt |
| 2003/0065250 A1 | 4/2003 | Chiel et al. |
| 2003/0088152 A1 | 5/2003 | Takada |
| 2003/0153866 A1 | 8/2003 | Long et al. |
| 2003/0214579 A1 | 11/2003 | Iddan |
| 2003/0225433 A1 | 12/2003 | Nakao |
| 2004/0106976 A1 | 6/2004 | Bailey et al. |
| 2004/0138689 A1 | 7/2004 | Bonutti |
| 2004/0204702 A1 | 10/2004 | Ziegler et al. |
| 2004/0243144 A1 | 12/2004 | Bonadio et al. |
| 2005/0154278 A1 | 7/2005 | Cabiri et al. |
| 2006/0021690 A1* | 2/2006 | Bunker ............... 152/419 |
| 2006/0089533 A1 | 4/2006 | Ziegler et al. |
| 2006/0241346 A1 | 10/2006 | Takada |
| 2006/0261771 A1 | 11/2006 | Anhalt et al. |
| 2006/0264707 A1 | 11/2006 | Kinney |
| 2006/0270901 A1 | 11/2006 | Bern et al. |
| 2007/0197868 A1 | 8/2007 | Takada |
| 2008/0045790 A1 | 2/2008 | Ziegler et al. |
| 2008/0183033 A1 | 7/2008 | Bern et al. |
| 2009/0227838 A1 | 9/2009 | Allen et al. |
| 2010/0198011 A1 | 8/2010 | Ziegler et al. |

FOREIGN PATENT DOCUMENTS

| | | | |
|---|---|---|---|
| JP | 58-041523 A | 3/1983 |
| JP | 59-125540 A | 7/1984 |
| JP | 60-030201 U | 3/1985 |
| JP | 61-137538 | 6/1986 |
| JP | 01-227737 A | 9/1989 |
| JP | 8-010102 | 1/1996 |
| JP | 8-038416 | 2/1996 |
| JP | 2000-033070 A | 2/2000 |
| JP | 2003-135386 A | 5/2003 |
| JP | 2004-226627 A | 8/2004 |
| WO | WO-96/00517 A1 | 1/1996 |
| WO | WO-99/51153 A2 | 10/1999 |
| WO | WO-01/06943 A1 | 2/2001 |
| WO | WO-01/37915 A2 | 5/2001 |
| WO | WO-03/041761 A2 | 5/2003 |
| WO | WO-2004/091689 A2 | 10/2004 |
| WO | WO-2006/126268 A1 | 11/2006 |
| WO | WO-2006/130422 A2 | 12/2006 |
| WO | WO-2007/043118 A1 | 4/2007 |
| WO | WO-2007/043123 A1 | 4/2007 |
| WO | WO-2007/050370 A2 | 5/2007 |
| WO | WO-2007/057962 A1 | 5/2007 |
| WO | WO-2007/057963 A1 | 5/2007 |

OTHER PUBLICATIONS

"International Application Serial No. PCT/US2010/002496, Written Opinion mailed Nov. 12, 2010", 9 pgs.

"U.S. Appl. No. 10/823,141, Amendment and Response filed Jun. 14, 2005" to Office Action mailed Mar. 15, 2005, 16 pgs.

"U.S. Appl. No. 10/823,141, Interview Summary mailed Jun. 27, 2005", 2 pgs.

"U.S. Appl. No. 10/823,141, Non-Final Office Action mailed Mar. 15, 2005", 5 pgs.

"U.S. Appl. No. 10/823,141, Notice of Allowance mailed Jul. 14, 2005", 3 pgs.

"U.S. Appl. No. 11/260,342, Final Office Action mailed Jan. 12, 2010", 6 pgs.

"U.S. Appl. No. 11/260,342, Non-Final Office Action mailed Oct. 26, 2009", 11 pgs.

"U.S. Appl. No. 11/260,342, Response filed Jan. 12, 2010 to Final Office Action mailed Jan. 12, 2010", 21 pgs.

"U.S. Appl. No. 11/260,342, Response filed Nov. 6, 2009 to Non-Final Office Action mailed Oct. 26, 2009", 29 pgs.

"U.S. Appl. No. 11/260,342, Response filed Aug. 27, 2009 to Restriction Requirement mailed Aug. 12, 2009", 24 pgs.

"U.S. Appl. No. 11/260,342, Restriction Requirement mailed Aug. 12, 2009", 11 pgs.

"U.S. Appl. No. 11/260,342, Notice of Allowance mailed Jan. 29, 2010", 6 Pgs.

"U.S. Appl. No. 11/825,528 Restriction Requirement mailed Aug. 17, 2010", 7 pgs.

"Canadian Application Serial No. 2522170, Office Action mailed Jun. 17, 2010", 2 pgs.

"Canadian Application Serial No. 2522170, Response filed Jul. 14, 2010 to Office Action dated Jun. 17, 2010", 4 pgs.

"European Application Serial No. 04750115.0, European Search Report mailed Dec. 18, 2009", 4 pgs.
"European Application Serial No. 04750115.0, Invitation to Proceed dated Jan. 4, 2010", 1 pg.
"European Application Serial No. 04750115.0, Office Action mailed Apr. 12, 2010", 10 Pgs.
"European Application Serial No. 04750115.0, Reply filed Mar. 3, 2010 to Office Actions of Dec. 18, 2009 and Jan. 4, 2010", 20 pgs.
"European Application Serial No. 06826140.3, Supplementary Partial European Search report mailed Jul. 16, 2009", 7 pgs.
"European Application Serial No. 06826140.3, Communication mailed Jun. 29, 2010", 4 pgs.
"European Application Serial No. 06826140.3, Response filed Oct. 13, 2009 to Communication dated Aug. 4, 2009", 8 pgs.
"Indian Patent Application No. 2625/CHENP/2005, First Examination Report mailed Jan. 9, 2007", 2 pgs.
"Indian Patent Application No. 2625/CHENP/2005, Second Examination Report mailed Jan. 7, 2008", 2 pgs.
"Indian Patent Application Serial No. 2625/CHENP/2005, First Examination Report mailed Jan. 9, 2007", 2 pgs.
"Indian Patent Application U.S. Appl. No. 2625/CHENP/2005, Response filed Jan. 9, 2008 to Second Examination Report mailed Jan. 7, 2008", 6 pgs.
"Indian Patent Application Serial No. 2625/CHENP/2005, Response filed Nov. 28, 2007 to First Examination Report mailed Jan. 9, 2007", 11 pgs.
"International Application Serial No. PCT US04/11466, Written Opinion mailed Apr. 15, 2005", 3 pgs.
"International Application Serial No. PCT/US04/11466, International Search Report mailed Apr. 14, 2005", 3 pgs.
"International Application Serial No. PCT/US2006/40617, International Search Report mailed Oct. 3, 2007", 4 pgs.
"International Application Serial No. PCT/US2006/40617, Written Opinion mailed Oct. 3, 2007", 12 pgs.
"International Application Serial No. PCT/US2006/040617, International Preliminary Report on Patentability mailed May 8, 2008", 12 pgs.
"International Application Serial No. PCT/US2009/004376, International Search Report mailed Apr. 29, 2010", 4 pgs.
"International Application Serial No. PCT/US2009/004376, Written Opinion mailed Apr. 29, 2010", 9 pgs.
"Israel Application Serial No. 170833, Office Action mailed Jan. 14, 2009", 4 pgs.
"Israel Application Serial No. 170833, Response filed May 11, 2009 to Office Action mailed Jan. 14, 2009", 4 pgs.

"Japanese Application No. 2006-510019, Office Action mailed Jan. 19, 2010", (w/ English Translation), 5 pgs.
"Japanese Application No. 2006-510019, Response filed May 13, 2010 to Office Action mailed Jan. 19, 2010", (w/ English Translation of Amended Claims), 13 pgs.
"Japanese Application Serial No. 2006-510019, Final Office Action mailed Jun. 8, 2010", (w/ English Translation), 4 pgs.
"Japanese Application Serial No. 2006-510091, Notice of Allowance mailed Aug. 31, 2010", 3 pgs.
"Mexican Application No. PA/a/2005/011024, Office Action", (2009), 3 pgs.
"Mexican Application Serial No. Pa/a/2005/011024, Response filed Oct. 20, 2008 to Office dated Aug. 15, 2008", 10 pgs.
"Singapore Patent Application No. 200506197-3, Examination Report dated Nov. 20, 2007", 4 pgs.
"Singapore Patent Application No. 200506197-3, Invitation to Respond to Written Opinion mailed Feb. 7, 2007", 4 pgs.
"Singapore Patent Application No. 200506197-3, Response filed Feb. 15, 2008 to Examination Report dated Nov. 20, 2007", 54 pgs.
"Singapore Patent Application No. 200506197-3, Response filed Jul. 3, 2007 to Invitation to Respond to Written Opinion mailed Feb. 7, 2007", 9 pgs.
"Singapore Patent Application No. 200506197-3, Response filed Jul. 3, 2007 to Office Action mailed Jul. 3, 2007", 9 pgs.
Ingram, M., et al., "Mechanics of the whole skin locomotion mechanism concentric solid tube model: the effects of geometry and friction on the efficiency and force transmission characteristics", *Proceedings of the IDETC/CIE 2006; ASME 2006 International Design Engineering Technical Conferences & Computers and Information in Engineering Conference*, (Sep. 10-13, 2006), (2006), 1-6.
Ingram, M. E., "Whole skin locomotion inspired by amoeboid motility mechanisms: mechanics of the cocentric solid tube model", *Masters Thesis*, Virginia Polytechnic Institute and State University, (2006), 48 pgs.
Kassim, I., et al., "Review of locomotion techniques for robotic colonoscopy", *Proceedings of the 2003 IEEE Internatinal Conference on Robotics and Automation*, (Taipei, Taiwan, Sep. 14-19, 2003), (Sep. 2003), 1086-91.
Phee, S J, "Locomotion and steering aspects in automation of colonoscopy", *IEEE Engineering in Medicine and Biology*, (Nov.-Dec. 1997), 85-96.
Office Action dated Feb. 5, 2013, issued by the European Patent Office in counterpart European Application No. 10757865.0.

* cited by examiner

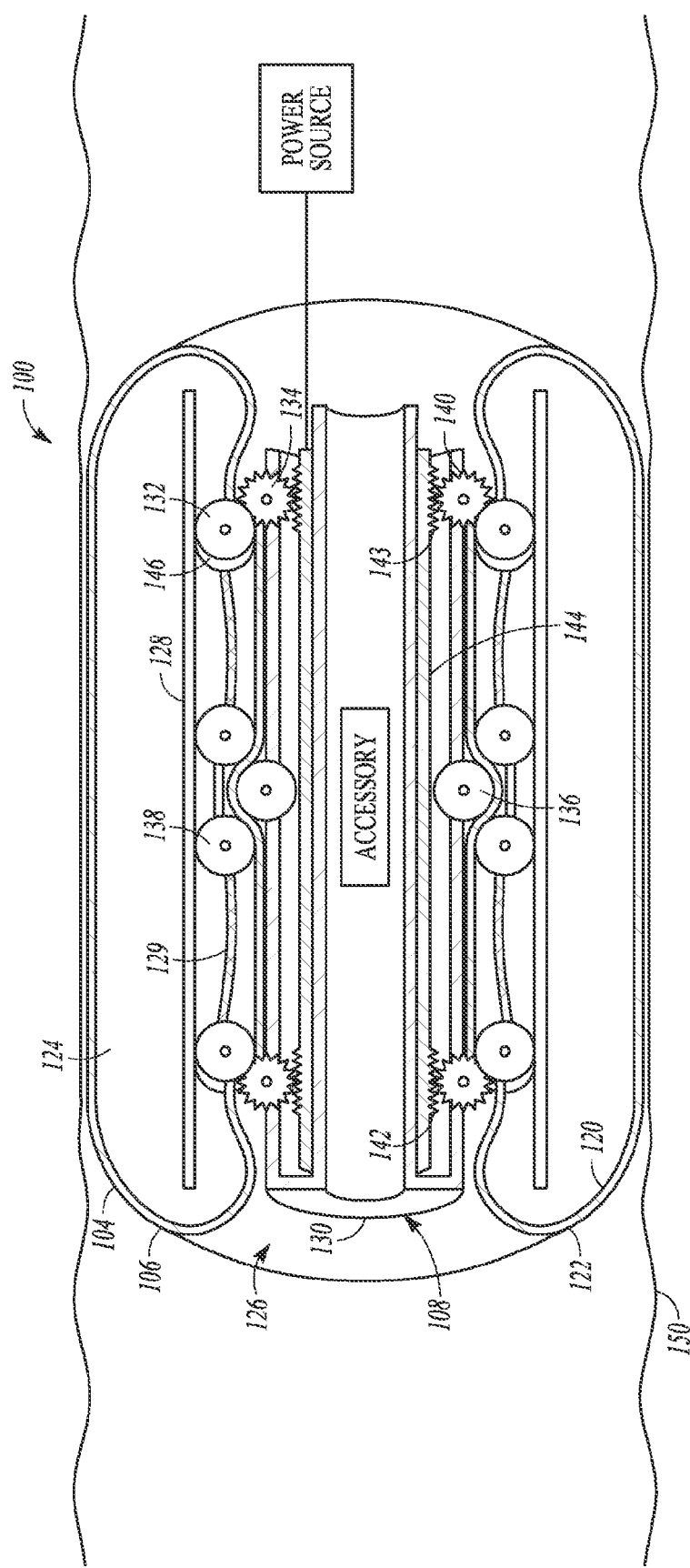

PROPELLABLE APPARATUS WITH ACTIVE SIZE CHANGING ABILITY

CLAIM OF PRIORITY

This non-provisional patent application claims the benefit of priority under 35 U.S.C. §119(e) to U.S. Provisional Patent Application Ser. No. 61/243,208 filed on Sep. 17, 2009, entitled "PROPELLABLE APPARATUS WITH ACTIVE SIZE CHANGING ABILITY," the specification of which is herein incorporated by reference in its entirety.

CROSS-REFERENCE TO RELATED APPLICATIONS

This patent document is related to U.S. application Ser. No. 10/823,141 (now U.S. Pat. No. 6,971,990), entitled "PROPULSION MECHANISM FOR ENDOSCOPIC SYSTEMS" filed on Apr. 13, 2004; U.S. application Ser. No. 11/260,342 (now U.S. Pat. No. 7,736,300), entitled "SELF-PROPELLABLE ENDOSCOPIC APPARATUS AND METHOD" filed on Oct. 27, 2005; and U.S. application Ser. No. 12/401,424 (published as U.S. Publication No. 2009/0227838), entitled "PROPELLABLE APPARATUS WITH PASSIVE SIZE CHANGING ABILITY" filed on Mar. 10, 2009, the specifications of which are hereby incorporated by reference in their entirety.

TECHNICAL FIELD

This patent document relates generally to propellable apparatus for use in medical or non-medical applications. Propellable apparatus can facilitate the introduction of one or more payload instruments into collapsible and non-collapsible body cavities or lumens, sections of pipe, and other generally tubular spaces or environments. More specifically, by not by way of limitation, this patent document relates to propellable apparatus including active size changing abilities.

BACKGROUND

Endoscopes are routinely used in medical procedures to view the interior of a patient's body and to facilitate treatment at sites inside the body as atraumatically as possible. Some common types of endoscopes include: colonoscopes, such as to view or treat the colon; enteroscopes, such as for use in the stomach or small bowel; and bronchoscopes, such as for use in the trachea or bronchi. Other payload instruments can also be useful when inserted into a body cavity or lumen, either with or without an accompanying endoscope.

OVERVIEW

Various approaches in facilitating the use of an endoscope or other medical or non-medical payload instrument include providing a propellable apparatus that can facilitate its introduction into or removal from a body cavity or lumen, section of pipe, or other generally tubular space or environment. Example approaches including a propellable apparatus are described in commonly-owned Ziegler et al. U.S. Pat. No. 6,971,990, entitled "PROPULSION MECHANISM FOR ENDOSCOPIC SYSTEMS," commonly-owned Ziegler et al. U.S. Pat. No. 7,736,300, entitled "SELF-PROPELLABLE APPARATUS AND METHOD," and commonly-owned Allen et al. U.S. Publication No. 2009/0227838, entitled "PROPELLABLE APPARATUS WITH PASSIVE SIZE CHANGING ABILITY." In some examples, a propellable apparatus can be mounted on the endoscope or other payload instrument. The propellable apparatus can propel or drive one or more rotatable membranes, such as one or more rotatable belt-like membranes, to create a propulsion force against a cavity or lumen wall. This propulsion force can aid in advancing or withdrawing the endoscope or other payload instrument.

The present inventors have recognized, among other things, that inflatable and deflatable support structures and related methods can be advantageous for changing a size, shape or compressibility of the one or more rotatable membranes of a propellable apparatus. The inflatable support structure can be selectively inflated to bias an outer surface of the one or more rotatable membranes outward to engage a cavity or lumen wall at a first outer diameter. The deflatable support structure can be selectively deflated and deformable inward, such as in response to a compressive force from a stricture in the cavity or lumen or in response to a command by an operator, to provide a membrane second outer diameter that is less than the first outer diameter. In various examples, the inflatable and deflatable support structures include a single, non-rotating bladder.

To better illustrate the propellable apparatus, methods and kits disclosed herein, a non-limiting list of examples is provided here:

In Example 1, a propellable apparatus comprises one or more rotatable membranes, sized and shaped to fit within and engage a cavity or lumen wall, the one or more rotatable membranes include an inner surface at least partially defining an encircled region and a continuous outer surface that turns outward to engage the cavity or lumen wall and turns inward to at least partially encompass a central region, wherein the one or more rotatable membranes are powerable to provide movement relative to the cavity or lumen wall in at least one of a forward or reverse direction; and an inflatable and deflatable support structure disposed within the encircled region, the support structure configured to inflate and bias the continuous outer surface of at least one rotatable membrane outward to engage the cavity or lumen wall at a first outer diameter, and configured to deform inward, through deflation, to provide a second outer diameter that is less than the first outer diameter.

In Example 2, the propellable apparatus of Example 1 is optionally configured such that the inflatable and deflatable support structure is configured to enable repeated inflation and deflation to provide varied outer diameters.

In Example 3, the propellable apparatus of at least one of Examples 1 or 2 is optionally configured such that the inflatable and deflatable support structure includes an impermeable bladder.

In Example 4, the propellable apparatus of at least one of Examples 1-3 is optionally configured such that the one or more rotatable membranes include at least two belt-like membranes.

In Example 5, the propellable apparatus of Example 4 optionally further comprises at least one web region configured to connect that at least two belt-like membranes.

In Example 6, the propellable apparatus of at least one of Examples 4 or 5 optionally further comprises inflation and deflation tubing used to inflate and deflate the inflatable and deflatable support structure, an end of the tubing is coupled to the support structure at a position between two of the belt-like membranes.

In Example 7, the propellable apparatus of at least one of Examples 4-6 optionally comprises a circumferential slit between the at least two belt-like membranes in alignment with the inflation and deflation tubing.

In Example 8, the propellable apparatus of Example 7 is optionally configured such that the inflatable and deflatable support structure includes a reduced outer diameter adjacent to the circumferential slit between the at least two belt-like membranes.

In Example 9, the propellable apparatus of at least one of Examples 1-8 optionally further comprises a frame including a drive support structure located within the encircled region and a housing structure located within the central region.

In Example 10, the propellable apparatus of Example 9 is optionally configured such that the inflatable and deflatable support structure does not rotate and is coupled, at least in part, to an outer surface portion of the drive support structure.

In Example 11, the propellable apparatus of at least one of Examples 1-10 optionally further comprises a pressure sensor configured to sense an internal pressure of the inflation and deflation support structure.

In Example 12, a kit comprises the propellable apparatus of at least one of Examples 1-11; and an endoscope coupled within the central region of the propellable apparatus.

In Example 13, a method comprises deploying one or more rotatable membranes and an inflatable or deflatable support structure within a cavity or lumen, the support structure is located within an encircled region defined by an inner surface of the one or more rotatable membranes; and at least one of, decreasing a diameter defined by an outer surface of the one or more rotatable membranes to a first diameter when a compressive force occurs within the cavity or lumen or through deflation of the support structure; or actively expanding the diameter of the outer surface of the one or more rotatable membranes to a second diameter, larger than the first diameter, through inflation of the support structure.

In Example 14, the method of Example 13 optionally comprises decreasing the diameter defined by the outer surface of the one or more rotatable membranes to the first diameter when a compressive force occurs within the cavity or lumen or through deflation of the support structure; and actively expanding the diameter of the outer surface of the one or more rotatable membranes to the second diameter, larger than the first diameter, through inflation of the support structure.

In Example 15, the method of at least one of Examples 13 or 14 is optionally configured such that actively expanding the diameter of the outer surface of the one or more rotatable membranes includes increasing a propulsive force generated between the outer surface of the rotatable membranes and a wall of the cavity of lumen.

In Example 16, the method of at least one of Examples 13-15 is optionally configured such that decreasing the diameter or actively expanding the diameter of the outer surface of the one or more rotatable membranes includes passing a stream of air or compressible gas through inflation or deflation tubing and into or out of the support structure.

In Example 17, the method of at least one of Examples 13-16 is optionally configured such that decreasing the diameter or actively expanding the diameter of the outer surface of the one or more rotatable membranes includes passing a stream of liquid through inflation or deflation tubing and into or out of the support structure.

In Example 18, the method of at least one of Examples 13-17 optionally further comprises propelling at least one payload instrument through the cavity or lumen using rotation of the one or more rotatable membranes.

In Example 19, the method of at least one of Examples 13-18 is optionally configured such that deploying the one or more rotatable membranes and the support structure within the cavity or lumen includes deploying the one or more rotatable membranes and the support structure through the colon and into the small bowel of a subject.

In Example 20, the method of at least one of Examples 13-19 optionally further comprises controlling an internal pressure of the support structure to a fixed pressure, including allowing the support structure to be vented when passing through a narrowing in the cavity or lumen.

These and other examples, advantages, and features of the present propellable apparatus, methods and kits will be set forth in part in the following Detailed Description. This Overview is intended to provide non-limiting examples of the present subject matter—it is not intended to provide an exclusive or exhaustive explanation. The Detailed Description is included to provide further information about the present propellable apparatus, methods and kits.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various embodiments discussed in the present patent document.

FIG. 1 illustrates a longitudinal cross-section of a propellable apparatus, in accordance with at least one embodiment.

DETAILED DESCRIPTION

Figure 2A:
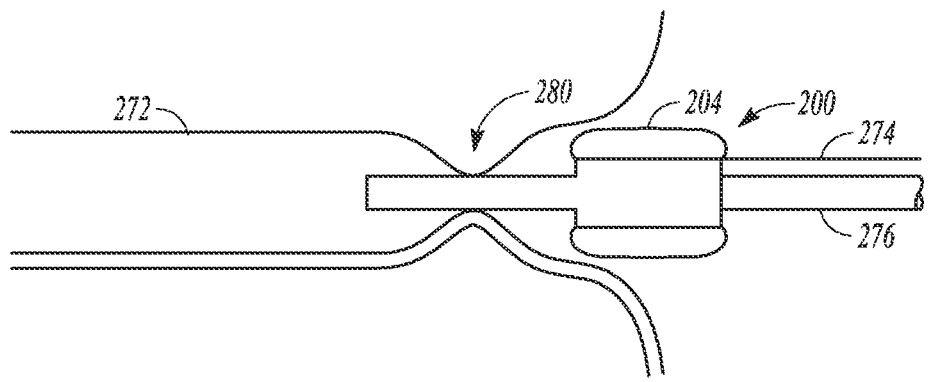
FIGS. 2A-2C illustrate a propellable apparatus within a cavity or lumen, in accordance with at least one embodiment.

One or more rotatable membranes, such as one or more rotatable belt-like membranes, can be used to create a propulsive force, such as between a propellable apparatus and the wall of a body cavity or lumen, or other generally tubular space or environment. The propellable apparatus can be used to help advance or maneuver an endoscope or other payload instrument, such as within the body cavity or lumen.

FIG. 1 illustrates a longitudinal cross-section of a propellable apparatus 100 that includes one or more rotatable membranes 104, as constructed in accordance with at least one embodiment. The one or more rotatable membranes 104 can be driven using an internal drive structure of the apparatus 100 to create a propulsive force with each continuous outer surface moving relative to a tissue cavity or lumen wall 150. In some examples, the one or more rotatable membranes 104 include a belt-like or ring-like shape. In some examples, the one or more rotatable membranes 104 include a toroidal shape. In various examples, the rotatable membranes 104 include a flexible material 106 having an interior surface 120 and a continuous exterior surface 122. The interior surface 120 of the flexible material 106 can at least partially define an interior volume or encircled region 124. The exterior surface 122 of the flexible material 106 can at least partially define a central cavity 126, as well as an outer diametrical size of the propellable apparatus 100.

The apparatus 100 can also include a frame 108. The frame 108 can be used to both support and interact with the flexible material 106 of the one or more rotatable membranes 104. In some examples, the frame 108 can include a drive support structure 128 and a housing structure 130. The housing structure 130 can be disposed in the central cavity 126. The drive support structure 128 can be disposed within the encircled region 124. In this example, the drive support structure 128 and the housing structure 130 can each rotatably support a plurality of rollers. For example, a plurality of motive rollers 134 are shown contacting a portion of the flexible material 106 of the one or more rotatable membranes 104. Rotation of the motive rollers 134 is capable of causing the flexible material 106 to move relative to the rotational axis of each motive roller 134.

The apparatus 100 can include a worm gear 144 having a first thread 142 and a second thread 143. The teeth 140 of a first set of motive rollers 134 can mate with the first thread 142 of the worm gear 144, such that rotation of the worm gear 144 will in turn cause the first set of motive rollers 134 to rotate. Similarly, the teeth 140 of a second set of motive rollers 134 can mate with the second thread 143 of the worm gear 144, such that rotation of the worm gear 144 will in turn cause the second set of motive rollers 134 to rotate. In some examples, the first thread 142 and the second thread 143 of the worm gear can form a single, longer thread that engages both sets of motive rollers 134.

The housing structure 130 can rotatably support a plurality of stabilizing rollers 136. Each stabilizing roller 136 can contact the exterior surface 122 of the flexible material 106 of the one or more rotatable membranes 104. A plurality of suspended stabilizing rollers 138 coupled to the drive support structure can be located proximate to each stabilizing roller 136 of the housing structure 130 and supported by one or more spring-loaded or other adjustable supports 129. Each suspended stabilizing roller 138 can contact the interior surface 120 of the flexible material 106 of the one or more rotatable membranes 104. In some examples, the suspended stabilizing rollers 138 can act to bias the exterior surface 122 of the flexible material 106 against a stabilizing roller 136.

A suspended motive roller 132 can be disposed proximate to each motive roller 134. Each suspended motive roller 132 can be pivotally supported by the drive support structure 128. In some examples, the drive support structure 128 and the suspended motive rollers 132 can act to bias the exterior surface 122 of the flexible material 106 against the motive rollers 134.

Various embodiments of the housing structure 130 and the drive support structure 128 are possible. In one example, the housing structure 130 and the drive support structure 128 can be viewed as two tubes positioned one inside the other. The outer tube can include the drive support structure 128, which can be located within the interior volume of the one or more rotatable membranes 104. The inner tube can include the housing structure 130, which can be located within the central cavity 126. In another example, either the drive support structure 128, the housing structure 130, or both can be comprised of a series of one or more beams that form a general shape, such as a cylinder. In another example, the drive support structure 128 and the housing structure 130 can be rigidly connected to one another or can have the spacing between them fixed by members angularly located in gaps between multiple rotatable belt-like membranes 104.

The flexible material 106 of the one or more rotatable membranes 104 can move between the housing 130 and drive support 128 structures. The distance between the two structures 128, 130 can be sufficient to accommodate one or more interlocking rollers or skids and to allow the flexible material 106 of each rotatable membrane 104 to pass, even if the material 106 folds over itself or is bunched up.

The present inventors have recognized that it can be beneficial to create a propulsive force for the outer or exterior surface 122 of the flexible material 106 in close proximity to a tissue cavity or lumen wall 150. In the case of a body cavity or lumen such as the colon or small bowel, for example, the present inventors have recognized that this propulsive force can increase as the diameter of the outer surface 122 of the flexible material 106 increases relative to the circumference of the body cavity or lumen wall 150. This increase in propulsive force may be driven by greater area of surface contact between the tissue cavity or lumen wall 150 and the rotating membrane 104 surfaces of the apparatus 100.

The propulsive force may also be increased due to increased contact pressure between the tissue cavity or lumen wall 150 and the rotating membrane 104 surfaces brought about by the increased diameter of the apparatus 100, specifically the one or more rotatable membranes 104. Yet, the present inventors have further recognized that having this relatively large diameter for increasing propulsive force is at odds with the desire to have as small of a diameter as possible for introducing the apparatus 100 (which can optionally be accompanied by an endoscope or other payload instrument) into the body cavity or lumen. Examples of orifices for introducing the endoscope and apparatus include the anal sphincter, or through the mouth, esophageal sphincter, and pylorus. In addition to these orifices and reduced-diameter sphincters, there can be other points of reduced lumen diameter, such as for example the iliocecal orifice between the small bowel and colon, or strictures in any of the body cavities such as brought on by scar tissue or growths such as cancers or polyps. These points of reduced diameter generally cannot accept introduction of rigid apparatus having diameters equal to the diameters of the internal lumens adjacent them without risk of injury or discomfort.

To attain the positive attributes of both a diametrically-larger and a diametrically-smaller propellable apparatus, the present inventors have conceived a propellable apparatus having variable diametrical capabilities, such as to accommodate extended use in one or more cavities or lumens of varying diameter. An example of this would be for an apparatus that is used to propel an endoscope or other payload instrument in a retrograde approach through the colon and into the small bowel. The colon typically has a diameter that can be 50-100% greater than a diameter of the small bowel. It is believed that a diametrically-variable propulsive apparatus can effectively propel the endoscope or other payload instrument through the larger diameter colon and then on into the smaller diameter small bowel.

One approach to providing some variability in diameter can be to use air or another compressible gas to inflate the flexible material. Another approach to providing diameter variability can be to use a liquid or other flowable material to inflate the flexible material. In various examples, the approaches to diameter variability include operator actuation once or multiple times or to multiple different diameters using the same propulsion apparatus during the same medical procedure. This can allow for operator-selected adjustment of the propellable apparatus diameter and selective tension adjustment of the one or more rotatable membranes.

Figure 2B:
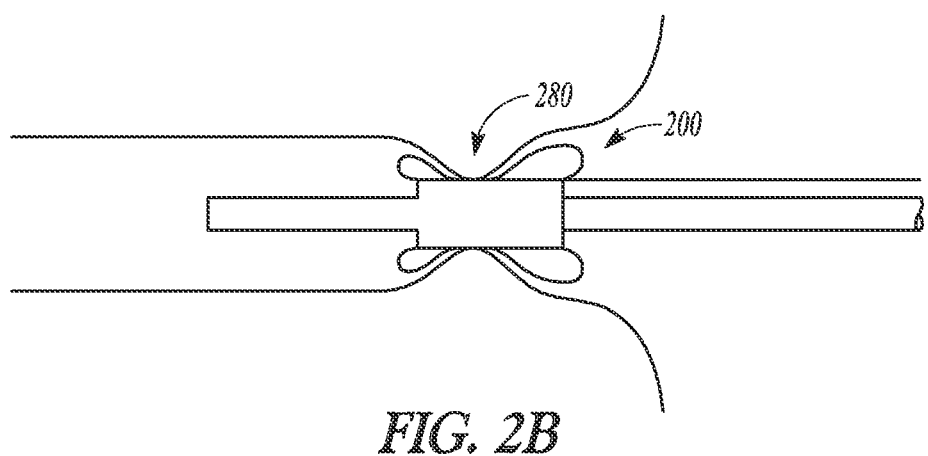
Figure 2C:
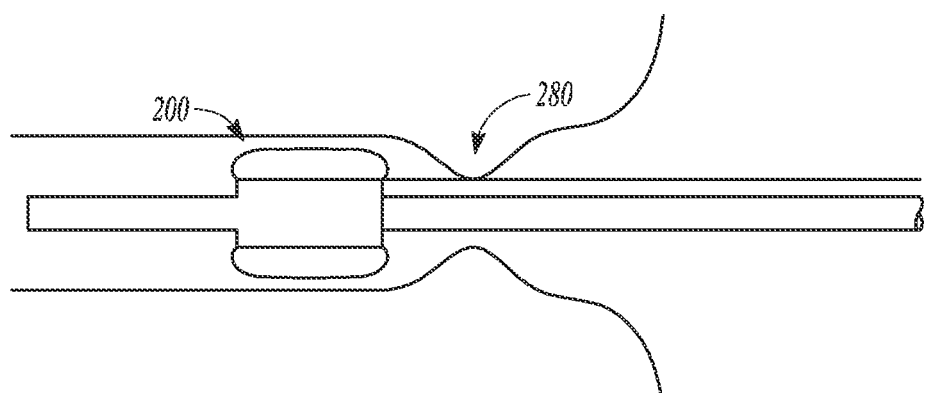

FIGS. 2A-2C illustrate a propellable apparatus 200 within a body cavity or lumen 272, in accordance with at least one embodiment. The propellable apparatus 200 can include one or more rotatable membranes 204, which can be driven by a drive mechanism as disclosed above, along with a drive cable 274, such as is described in commonly-owned Sheridan et al. U.S. Publication No. 2009/0233747, entitled "TORQUE-ADJUSTING DRIVE MECHANISM FOR A PROPELLABLE DEVICE," the disclosure of which is incorporated by reference herein in its entirety.

As shown, the propellable apparatus 200 can carry an endoscope or other payload instrument 276 within the body cavity or lumen 272. Depending on whether the propellable apparatus 200 is to be used for medical or non-medical applications, the payload instrument 276 can be selected from a group consisting of endoscopes, cameras, video processing circuitry, fiber optic cables, electronic communication cables, lasers, surgical instruments, medical instruments, diagnostic instruments, instrumentation, sensors, stent catheters, fluid delivery devices, drug delivery devices, electronic devices, tools, sampling devices, assay devices, articulating segments, cables to articulate the articulating segments, other payload instruments, and combinations thereof.

In various examples, the propellable apparatus 200 can include a deflatable support structure, such as an impermeable bladder configured to compress or be actively deflated to a smaller diameter when the propellable apparatus 200 passes through a sphincter or other region of reduced diameter 280, as shown in the example of FIG. 2B. The propellable apparatus 200 can also include an inflatable support structure configured to expand or be actively inflated back to its original or an expanded diameter after passing through the region of reduced diameter 280, as shown in the example of FIG. 2C. In some examples, one or more of these inflatable or deflatable support structures can be mounted to the outer surface of the rigid drive mechanism, specifically the drive support structure 128, such that the flexible material 206 of the one or more rotatable membranes 204 slide over their outer surfaces when the drive mechanism is engaged to drive the flexible material 206. In various example, the deflatable support structure and the inflatable support structure are integrated with each other in the form of an impermeable bladder.

Figure 3:
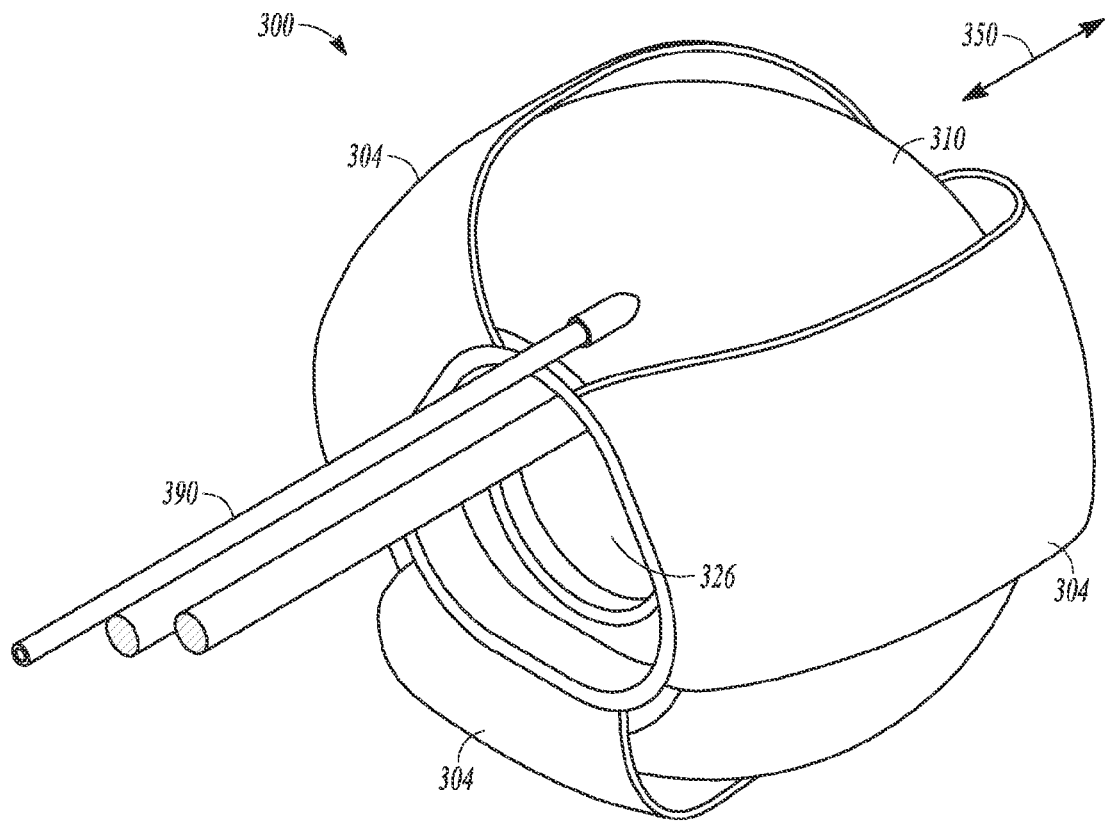
FIG. 3 illustrates a propellable apparatus including an inflatable and deflatable support structure, in accordance with at least one embodiment.

FIG. 3 illustrates an isometric view of a propellable apparatus 300 including one or more rotatable membranes 304 and at least one inflatable and deflatable support structure 310, in accordance with at least one embodiment. Actuated rotation, such as can be controlled by an operator, of the membranes 304 can assist in advancing an endoscope or other payload instrument coupled within a central cavity 326 through body cavities or lumens. The one or more rotatable membranes 304 can provide enhanced contact with a cavity or lumen wall through inflation of the inflatable and deflatable support structure 310, such as an impermeable bladder, located within and which acts to expand the rotatable membranes 304. As shown, the one or more rotatable membranes 304 can form a continuous loop parallel or substantially parallel with a driven direction of travel 350.

In the example of FIG. 3, the at least one inflatable and deflatable support structure 310 can include a single toroidal bladder that does not rotate and that is mounted, in part, to an outer surface of a rigid drive support structure located inside the loop of the one or more rotatable membranes 304. The one or more rotatable membranes 304 can include three or more rotatable belt-like membranes, for example. These belt-like membranes can be configured to pass through the annular space between the rigid drive support (located inside the loop of the membranes) and a housing structure (located in the central cavity 326), as further discussed above. In this space, the belt-like membranes can be driven by one or more gears or rollers attached to the drive support structure or the housing structure. The belt-like membranes can then pass out and over the inflatable and deflatable toroidal bladder. The outer surfaces of the belt-like membranes can be opposed to the tissue wall of the body cavity or lumen as they rotate out and over the toroidal bladder, thereby propelling the apparatus 300 in one of a forward or reverse direction along the direction of travel 350.

The traction these belt-like membranes can gain against the tissue cavity or lumen wall can be enhanced by increasing the normal force of one or more of the membranes against the tissue cavity or lumen wall. This normal force can be increased by inflating the toroidal bladder to press one or more of the belt-like membranes against the tissue cavity or lumen wall. The inflation and deflation tubing 390 used to inflate and deflate the bladder can be positioned between two of the belt-like membranes. In some examples, having the tubing 390 permanently attached to the toroidal bladder can be beneficial, as it can allow the pressure to be regulated continuously during operation of the propellable apparatus 300. In some examples, the propellable apparatus 300 can have its inflation pressure controlled to a fixed level (fixed pressure of the toroidal bladder as opposed to fixed volume). Using a fixed pressure, the toroidal bladder can be allowed to be vented by a controller when the propellable apparatus 300 passes through a narrowing in the cavity or lumen anatomy so that the diameter of the apparatus 300 reduces to match the diameter of the anatomy while still maintaining the same bladder pressure and resulting normal force of the one or more belt-like membranes against the tissue cavity or lumen wall. Similarly, air or other fluid can be added by the controller when the anatomic diameter increases to fill the toroidal bladder back up.

Figure 4A:
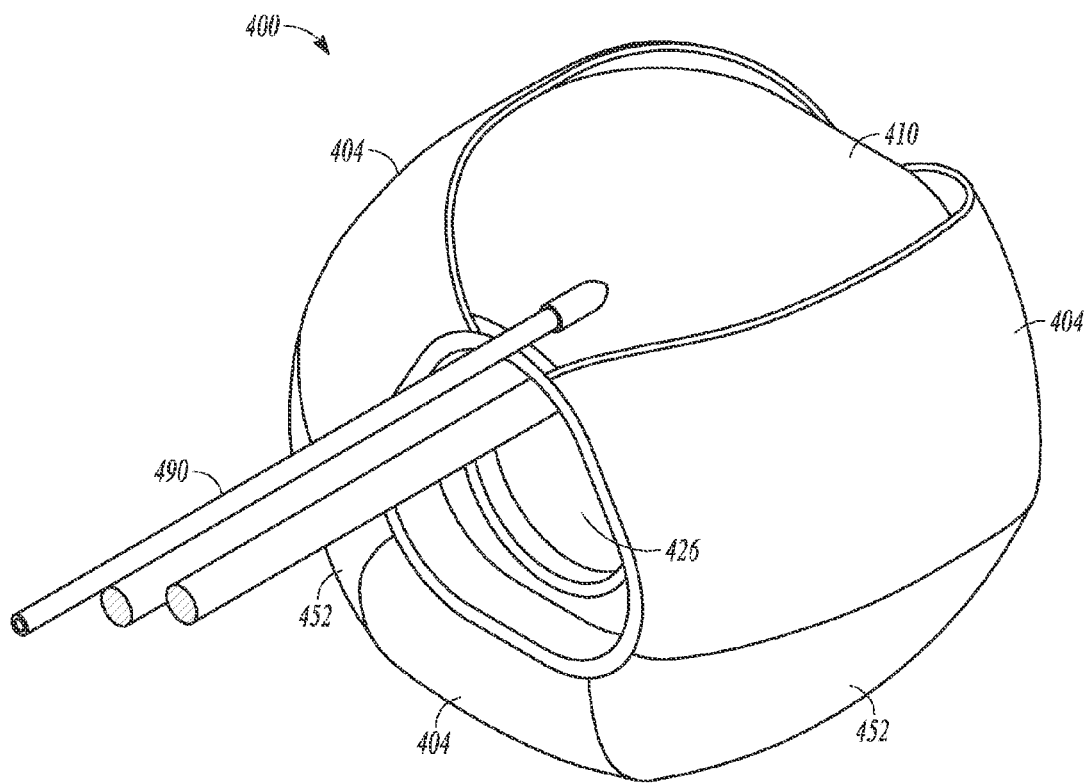
FIGS. 4A-4B illustrate another propellable apparatus including an inflatable and deflatable support structure, in accordance with at least one embodiment.
Figure 4B:
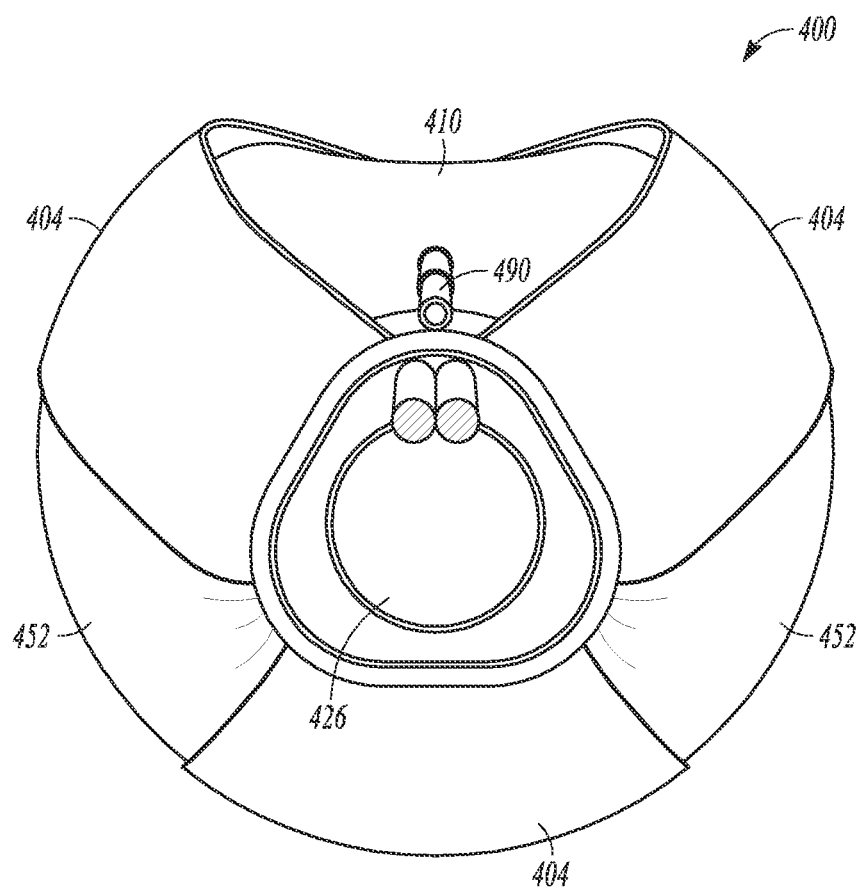

FIGS. 4A and 4B illustrate an isometric view of a propellable apparatus 400 including one or more rotatable membranes 404 and at least one inflatable and deflatable support structure 410, in accordance with at least one embodiment. Actuated rotation, such as can be controlled by an operator, of the membranes 404 can assist in advancing an endoscope or other payload instrument coupled within a central cavity 426 through body cavities or lumens. The one or more rotatable membranes 404 can provide enhanced contact with a cavity or lumen wall through inflation of the inflatable and deflatable support structure 410, such as an impermeable bladder, located within and which acts to expand the rotatable membranes.

Figure 5:
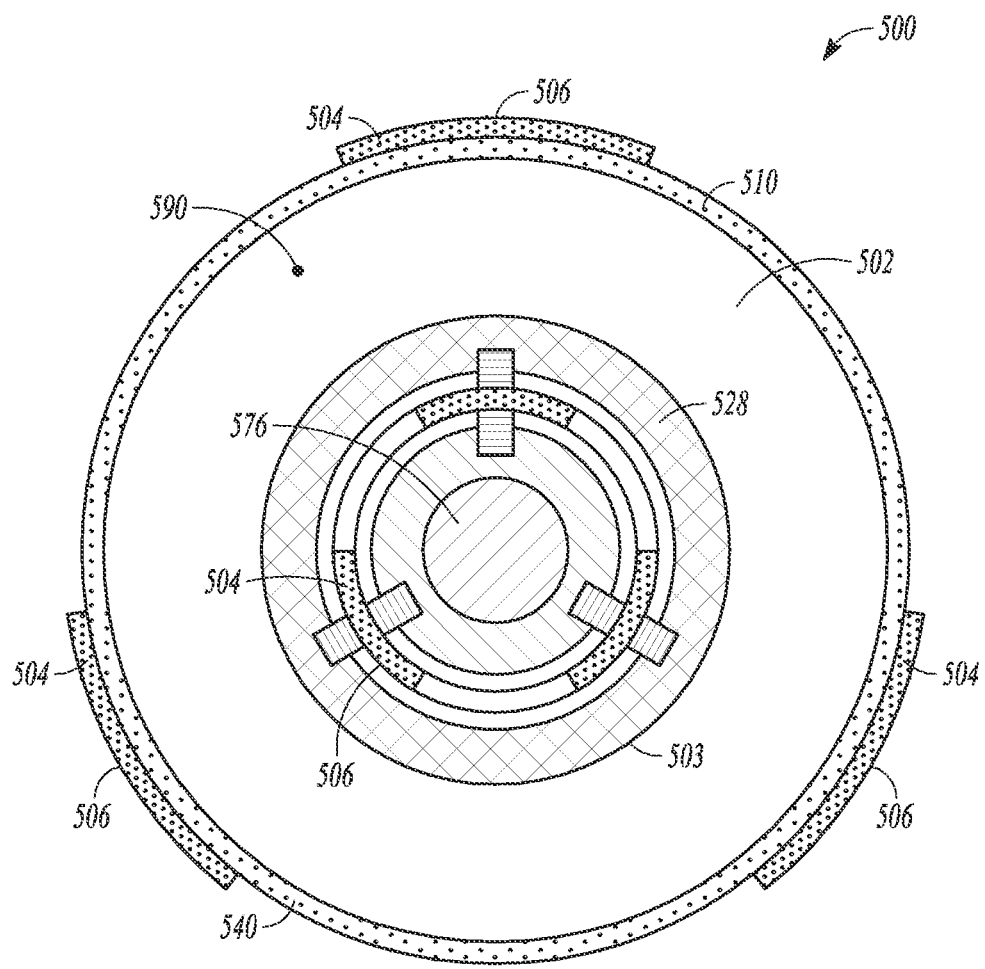
FIG. 5 illustrates a transverse cross-section of a propellable apparatus including an inflatable and deflatable support structure, in accordance with at least one embodiment.

In the example of FIGS. 4A and 4B, the propellable apparatus 400 can include a single toroidal bladder that does not rotate and that is mounted, in part, to longitudinal end portions of a rigid drive support structure located inside the loop of the rotatable membranes 404. As shown, the propellable apparatus 400 can include three or more rotatable belt-like membranes, which as shown in FIG. 5, can be aligned with internal drive gears attached to the rigid drive support structure or a housing structure. In some examples, there can be two thin-walled, membrane web regions 452 connecting the three thicker-walled belt-like membranes. In this way, there can be one acting rotatable membrane, which is a continuous loop in its longitudinal rotating axis, and which includes a slit between two of the belts circumferentially. This slit can provide a path for an inflation and deflation tube 490 to be coupled to the toroidal bladder without disturbing the rotation of the membrane. As shown, and in some examples, the toroidal bladder can have a reduced outer diameter aligned with the slit in the outer rotating membrane. As a result, only the non-slit rotating surface of the membrane can be in pressurize contact with the tissue wall of the body cavity or lumen. It is believe that this can improve the efficiency of the propulsive drive of the apparatus 400, since non-rotating bladder surfaces in the areas of slits in the membrane surfaces can add drag to the desired propelled motion of the apparatus 400 if such non-rotating surfaces were in contact with the cavity or lumen wall tissue.

FIGS. 4A and 4B illustrate propellable apparatus 400 having only one slit or gap in the rotating membrane corresponding to the connection of the inflation and deflation tube 490 to the inflatable and deflatable bladder 410. It is also possible to have multiple slits or gaps in the membrane with corresponding reduced bladder diameters aligned with these slits or gaps. As one example, the propellable apparatus 400 including three belt-like membranes 404 can lack web regions 452 connecting these membranes to one other and, as such, the inflatable and deflatable bladder 410 can include three areas of reduced diameter positioned between the three belt-like membranes 404. In such an example, the belt-like membranes 404 can be driven by motive rollers coupled to a common worm gear resulting in the input drive speed for each belt being the same. By not having the belt-like membranes 404 connected with one or more web regions 452, different amounts of slip of the membranes 404 over the motive rollers can, in some examples, be better tolerated as each belt can run at slightly different speeds without the one or more web regions 452 between these belts wrinkling and binding.

Some of the believed advantages of a variable diameter, propellable apparatus such as is shown in FIGS. 3-5 include, but are not limited to, easily maintaining a uniform radial pressure, minimal mass for the size altering mechanism which can help to keep the overall diameter of the apparatus small for passage through constrained regions of the anatomy, the ability to operate in either a passive control mode (i.e., fixed pressure), or allow the operator to select pressure at their discretion during a procedure. Other configurations of this same concept can be possible including multiple inflatable and deflatable support structures (e.g., bladders), paired bladders and belts, inflation from the inner wall of a bladder against a cylindrical frame component, and others which utilize bladder expansion control of the rotating propulsive surfaces for an endoscopic or other payload assist device. Additionally, the one or more rotatable membranes 404 (e.g., belts) can optionally include teeth or other embedded grip mechanisms on an outer surface of the flexible material, such as teeth matable with teeth of a motive drive gear. Other options include varying the thickness, stiffness, texture, surface finish, surface pattern, durometer, flexibility, durability, friction characteristics, color, hydrophilic/hydrophobic tendencies, elasticity, wear characteristics, permeability, melting point, biocompatibility, chemical compatibility or chemical solubility of the flexible material of the membranes 404 or the inflatable and deflatable support structure 410.

FIG. 5 illustrates a transverse cross-section of a propellable apparatus 500 including one or more rotatable membranes 504 and at least one inflatable and deflatable support structure 510, in accordance with at least one embodiment. An endoscope or other payload instrument 576 can be coupled to the propellable apparatus 500. In this example, the inflatable and deflatable support structure 510 can include an impermeable bladder or other similar material 540 that can be attached to an outer surface 503 of a rigid drive support structure 528 and is located within an encircled region 502 of the propellable apparatus 500 between an outer surface 503 of the rigid drive support structure 528 and a surface of a flexible material 506 of the rotatable membranes 504. In some examples, the impermeable bladder 540 can be attached at or near opposite longitudinal ends of the drive support structure 528. These attachments can be fixed or in respective slide track mechanisms (such as to allow a degree of axial movement).

In one example, the propellable apparatus 500 is an apparatus designed for use over a 9 millimeter diameter enteroscope and the rigid drive support structure 528 can have an outer diameter of about 17 millimeters. In such an example, the impermeable bladder 540 can be adhered to the outer surface of the rigid drive support structure 528 to yield an effective original or expanded outer diameter of about 32 millimeters. An example of a possible impermeable bladder material 540 that can be used is 85A Polyether Aromatic Polyurethane, which is produced by Stevens Urethane, of Easthampton, Mass. As shown, the flexible material 506 of the rotatable membranes 504 can traverse through the internal drive structure of the apparatus 500 and wrap over the outer surface of the impermeable bladder 540. In some examples, the inflatable and deflatable support structure 510 allows a 32 millimeter drive diameter, while compressing down to a diameter of 18 millimeters or less when passing through regions of reduced diameter. A size of the inflatable and deflatable support structure 510 can be manipulated using an inflation and deflation tube 590 sealed to the impermeable material of the bladder 540. Advantageously, the deflatable space provided through the use of a bladder 540 can permit for greater size deformations than may be possible if such space was filled or partially filled with a solid structure.

Optionally, the thickness of the impermeable bladder 540 and the stiffness of the material used for the impermeable bladder 540 can be varied, such as to strike a desired balance between the desired compressed diameter for passing through a restricted body cavity or lumen diameter, the desired compressive force for compressing the bladder 540 to the restricted diameter, and the desired expansive force of the bladder 540 for providing the propulsive force at the flexible material 506 when the inflatable and deflatable bladder in a partially or fully expanded state within the body cavity or lumen. The diameters cited above are provided by way of illustrative example, and not by way of limitation. Other sizes of endoscopes or other payload instruments, and other diameters of the rigid drive support structure of a propellable apparatus can be used as desired, such as for different anatomies, while still using and benefiting from an actively expandable and compressible structure to conform to different anatomical sizes in use.

Closing Notes:

The present inventors have conceived a propellable apparatus having an outer diameter, which is configured to be variable, such as to allow a smaller diameter when passing through points or regions of reduced diameter, and to allow a larger drive diameter in larger diameter regions of a cavity or lumen. The examples described herein enable a number of possible structures that can achieve a variable rotatable membrane diameter for the propellable apparatus, which can be used to propel or maneuver an endoscope or other payload instrument through a varying diameter cavity or lumen. Other materials or variations of these examples can be used, such as to achieve a desired variable diameter, which can benefit the performance of the propulsion apparatus.

Advantageously, the present propellable apparatus include one or both of an inflatable or deflatable support structure that can selectively fill the volume or a portion of the volume of the diameter between (1) the outer diameter of the rigid drive mechanism, specifically the drive support structure, that helps drive the flexible material of the one or more rotatable membranes; and (2) the desired outer diameter of the flexible material that provides propulsion in a cavity or lumen. These inflatable and deflatable support structures can provide support or a lack of support, as needed, when the propellable apparatus traverses a varying diameter cavity or lumen.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

The above Detailed Description is intended to be illustrative, and not restrictive. For example, the above-described apparatus examples (or one or more aspects thereof) may be used in combination with each other. Other embodiments can be used, such as by one of ordinary skill in the art upon reviewing the above description. The present inventors recognize that in a field different from medical applications, the present propellable apparatus can be used in non-medical or commercial and industrial applications to obtain views, for examples, from non-body cavities or lumens, such as sections of pipe or other structures having a number of curves and turns. Such cavities or lumens can be partially occluded or have build-up on an inner surface and thus present an irregular internal shape or diameter impeding advancement of the viewing or other payload instrument carried by the propellable apparatus. For applications of a non-medical nature, the materials used in the apparatus do not necessarily require biocompatibility or sterilization tolerance, as can be typical for medical applications.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "including" and "comprising" are open-ended, that is, a system, device, apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A propellable apparatus comprising:
   one or more rotatable membranes, sized and shaped to fit within and engage a cavity or lumen wall, the one or more rotatable membranes comprising an inner surface at least partially defining an encircled region and a continuous outer surface that turns outward to engage the cavity or lumen wall and turns inward to at least partially encompass a central region, wherein the one or more rotatable membranes are powerable to provide movement relative to the cavity or lumen wall in at least one of a forward or reverse direction;
   an inflatable and deflatable support structure disposed within the encircled region, the support structure configured to inflate and bias the continuous outer surface of at least one rotatable membrane outward to engage the cavity or lumen wall at a first outer diameter, and configured to deform inward, through deflation, to provide a second outer diameter that is less than the first outer diameter;
   an inflation and deflation tubing used to inflate and deflate the inflatable and deflatable support structure; and
   a frame including a drive support structure located within the encircled region and a housing structure located within the central region,
   wherein the inflatable and deflatable support structure does not evert while the one or more rotatable membranes are being revolved about the drive support structure and is coupled, at least in part, to an outer surface portion of the drive support structure.

2. The propellable apparatus of claim 1, wherein the inflatable and deflatable support structure is configured to enable repeated inflation and deflation to provide varied outer diameters.

3. The propellable apparatus of claim 1, wherein the inflatable and deflatable support structure includes an impermeable bladder.

4. The propellable apparatus of claim 1, wherein the one or more rotatable membranes include at least two belt-like membranes.

5. The propellable apparatus of claim 4, further comprising at least one web region connecting the at least two belt-like membranes.

6. The propellable apparatus of claim 4, wherein an end of the tubing is coupled to the support structure at a position between two of the belt-like membranes.

7. The propellable apparatus of claim 6, comprising a circumferential slit between the at least two belt-like membranes in alignment with the inflation and deflation tubing.

8. The propellable apparatus of claim 7, wherein the inflatable and deflatable support structure includes a reduced outer diameter adjacent to the circumferential slit between the at least two belt-like membranes.

9. The propellable apparatus, as claim in claim 8, wherein the tubing is attached to the inflatable and deflatable support structure having the reduced outer diameter from the side thereof.

10. The propellable apparatus of claim 1, further comprising a pressure sensor configured to sense an internal pressure of the inflation and deflation support structure.

11. A kit comprising:

the propellable apparatus of claim 1; and an endoscope coupled within the central region of the propellable apparatus.

\* \* \* \* \*